United States Patent [19]

Paparatto et al.

[11] Patent Number: 4,788,354

[45] Date of Patent: Nov. 29, 1988

[54] METHOD FOR THE SYNTHESIS OF IODOBENZENE

[75] Inventors: Giuseppe Paparatto, Cinisello Balsamo; Marco Saetti, Priolo, both of Italy

[73] Assignee: Montedipe S.p.A., Milan, Italy

[21] Appl. No.: 19,630

[22] Filed: Feb. 27, 1987

Related U.S. Application Data

[63] Continuation-in-part of Ser. No. 786,483, Oct. 11, 1985.

[30] Foreign Application Priority Data

Oct. 16, 1984 [IT] Italy ................................ 23169 A/84

[51] Int. Cl.$^4$ ............................................. C07C 17/15
[52] U.S. Cl. .................................... 570/203; 570/206; 570/208
[58] Field of Search ............... 570/206, 208, 203, 202, 570/204

[56] References Cited

U.S. PATENT DOCUMENTS

| | | | |
|---|---|---|---|
| 3,363,010 | 1/1968 | Schwarzenbek | 570/203 |
| 3,600,331 | 8/1971 | Ingwalson | 570/203 |
| 3,644,542 | 2/1972 | Prahl et al. | 570/203 |
| 4,240,987 | 12/1980 | Martin et al. | 570/206 |
| 4,391,785 | 7/1983 | Rosinski et al. | 502/77 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/206 |
| 77631 | 5/1982 | Japan | 570/206 |
| 149496 | 12/1963 | U.S.S.R. | 570/206 |

OTHER PUBLICATIONS

Groggins, "Unit Processes in Organic Chemistry", (1958) Fifth ed., McGraw-Hill Book Co. Inc. p. 262.

*Primary Examiner*—Werren B. Lone
*Attorney, Agent, or Firm*—Stevens, Davis, Miller & Mosher

[57] ABSTRACT

A method for the synthesis of iodobenzene by iodination, in the gaseous phase, of benzene with iodine, in the presence of a zeolitic catalyst, selected from the group comprising the zeolites of X type or of Y type, characterized in that said iodination is an oxidative one and that said zeolites are in a form different from the acid (H) form.

11 Claims, No Drawings

METHOD FOR THE SYNTHESIS OF IODOBENZENE

RELATED APPLICATIONS

This application is a continuation-in-part of Ser. No. 786,483 filed Oct. 11, 1985, which is herein incorporated by reference in its entirety.

BACKGROUND OF THE INVENTION

The synthesis of iodobenzene starting from benzene and iodine is usually carried out in a liquid phase, in the presence of an oxidative agent; preferably the oxidative action is carried out by nitric acid (see Japanese Pat. No. 58/77830, U.S.S.R. Pat. No. 453392 and an article of Datta R. L. and Chatterjee N. R. on the J. Am. Chem. Soc., 39, 437, 1917). Other oxidative agents may be also used as well; none of them, however, has proved, hitherto, to be more efficient and convenient. For instance, iodic acid, sulphur trioxide and hydrogen peroxide were used (see Butler A. R.: J. Chem. Educ. 36, 508, 1971) and the iodination catalyzed by metal halogenides was reported as well (see Uemura A., Onoe A., Okano M., Bull. Chem. Soc. Jpn. 47, 147, 1974). Japanese patent publication No. 82/77631 teaches the direct iodination of benzene in the gaseous phase and in the presence of 13 X zeolites, but excludes absolutely the need of adding $O_2$ or any other oxidizing agent. Recently, Italian patent publication No. 19860 A/84, in the name of the Applicant, describes a process for the synthesis of aromatic iodo-substituted compounds starting from alkaline salts of aromatic acids, by reaction with iodine. In all the well known methods, the selectivities to iodine are never higher than 90%; in a few methods use is made of expensive oxidative agents and in other methods one starts from not very available reactants. Now we have found that the synthesis of iodobenzene can be carried out more conveniently accordingly to the reaction:

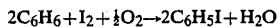

$$2C_6H_6 + I_2 + \tfrac{1}{2}O_2 \rightarrow 2C_6H_5I + H_2O \quad (I)$$

using $O_2$ as oxidative agent and a particular zeolite as catalyst.

DISCLOSURE OF THE INVENTION

In its most general form, the invention relates to a method for the synthesis of iodobenzene in a gaseous phase, by iodination of benzene with iodine, in the presence of zeolites of the X or Y type, characterized in that the iodination is carried out in the presence of $O_2$, air or other molecular containing gas and in that the zeolites are used in a form different from the acid (H) form. In detail: a gaseous mixture of benzene, iodine and oxidizing gas is conveyed onto a catalyst based on zeolites of 13 X type or of Y type in non-acid form. The catalysts may be used as such or mixed with a suited amount of an inert agent, for instance $SiO_2$, acting as a binder and/or as carrier.

The X or Y zeolites have to be used in the form exchanged with monovalent or trivalent cations, and in particular with alkaline or rare-earth cations. If use is made of a zeolite exchanged with a mono- or trivalent metal cation, a stabilization of the catalytic activity will be noted; should, on the contrary, zeolites be used in their acid form, a decay of the catalytic activity will be noted. Moreover, in the case of zeolites having a low ($\leq 10$) $SiO_2/Al_2O_3$ ratio, the acid form can not be used, as a structure collapse takes place under the reaction conditions and during the optional reactivation.

According to a preferred embodiment of the invention the system consists of a 13 X or NaY zeolite.

The catalytic system can also consist of zeolites exchanged with two or more metal cations. For instance, the sodium of the sodic form can be exchanged partly with another metal cation. Cobalt and the rare earth metals are illustrative of such metal cations. The same type of catalyst can also be prepared starting from the acid form of the zeolite, carrying out first a partial exchange of the proton with the desired metal cation, using the solution of a hydrosoluble salt thereof; thereafter the residual acid sites can be neutralized by means of a diluted solution of NaOH or KOH. When this latter technique is used, a completely exchanged catalyst is obtained and all the Bronsted acid sites, which are responsible for the decay of the catalytic activity, are eliminated.

The iodination can be carried out according to the most different techniques, without swerving from the spirit of the invention; by way of example, however, the following general recommendations are advisable. A benzene iodine molar ratio of 10 to 30 is generally advisable. In practice, iodine solution in benzene (concentration from 0.5 to 50% by weight, preferably from 5 to 20% by weight) is evaporated and mixed with air, or other gas containing oxygen, in such an amount that, in the case of the oxygen containing gas being air, the air/$I_2$ molar ratio is preferably higher than, but in all cases at least equal to, the stoichiometric one and preferably $\geq 10$. The resultant mixture is conveyed to a fixed bed reactor, loaded with the catalyst, the temperature ranging between 200° and 550° C. (preferably between 200° and 500° C., more preferably between 250° and 450° C.) and the space velocity (WHSV) ranging between 0.1 and 100 (preferably between 1 to 20, more preferably between 12 and 20) Kg/h of benzene per Kg of active part (pure zeolite, binder excluded); use may also be made of an inert diluent such as, for instance, nitrogen, helium or steam. The products can be then recovered by cooling the gaseous flow leaving the reactor and by resorting to usual treatments. In case of distillation, the overhead distilled benzene can be recycled to the iodination reactor. The global pressure used during the tests is almost always slightly higher than the atmospheric one; however, lower or higher pressures may be used. The catalyst maintains its activity a long time, particularly when one works, in a gas phase, at 250°–450° C.; however, when the catalytic activity falls below the allowable levels, one starts the regeneration. An excellent regeneration consists in activating the catalyst in benzene-air mixtures for a few hours at temperatures from 300° to 600° C. The starting activation of the catalyst is an important element as well.

The following examples illustrate the invention, without limiting, however, the scope thereof.

EXAMPLE 1 (NaY)

1 g of a NaY zeolite, produced by Union Carbide Company, was loaded into a quartz microreactor, kept at 400° C. by means of a thermostat and continuously fed with a gaseous mixture of benzene, iodine and air, with a benzene:iodine:air molar ratio=20/1/20. The pressure was slightly higher than the atmospheric pressure and the space velocity (WHSV) was 6 Kg/h of benzene/iodine mixture per Kg of zeolite. The reaction went on for 6 hours; the reaction products were gathered by condensation. The iodine conversion was 100%, the molar selectivity to iodobenzene 97.5%, to diiodobenzene 2.3% and to others 0.2%.

Data and results are set forth in Table 1, wherein the term "selectivity" means the molar selectivity to benzene.

EXAMPLE 2 (13X)

Example 1 was repeated, using a 13X zeolite sold by Davison Company as catalyst. Data and results are set forth in Table 1.

EXAMPLE 3

Example 2 was repeated, lowering the temperature 325° C.; data and results are set forth in Table 1.

EXAMPLE 4-15

Examples 2 and 3 were repeated, varying the temperature and the space velocity, as indicated in Table 1, that shows the obtained results as well. The 13X zeolite used was produced by Union Carbide Company.

EXAMPLE 16

In order to demonstrate the incidence of space velocity, namely of the contact time, example 10 was repeated, increasing the space velocity to 22.8 $h^{-1}$, thereby obtaining the following results, which are undoubtedly less satisfactory:

|  | After 1 hour | After 6 hours |
|---|---|---|
| $I_2$ conversion = | 97% | 30% |
| Selectivity to: |  |  |
| Iodobenzene | 96.1% | 94.0% |
| Diiodobenzene | 3.9% | 6.0% |

COMPARATIVE EXAMPLES 17 AND 18; AND EXAMPLE 19

Example 1 was repeated, varying slightly the space velocity and replacing the NaY zeolite with the zeolites indicated in Table 1, the Table showing the obtained results. It will of course be understood that under the prevailing oxidative conditions the $Co^{++}$ of Example 19 will be converted to $Co^{+++}$.

TABLE 1

| Ex. | Zeolite | T (°C.) | WHSV ($h^{-1}$) | Conv. $I_2$ (%) 1 h | Conv. $I_2$ (%) 6 h | Selectivity (%) $C_6H_5I$ 1 h | $C_6H_5I$ 6 h | $C_6H_4I_2$ 1 h | $C_6H_4I_2$ 6 h | others 1 h | others 6 h |
|---|---|---|---|---|---|---|---|---|---|---|---|
| 1 | Na Y (a) | 400 | 6 | — | 100 | — | 97.5 | — | 2.3 | — | 0.2 |
| 2 | 13 X (b) | 400 | 6 | — | 100 | — | 97.0 | — | 2.8 | — | 0.2 |
| 3 | 13 X (b) | 325 | 6 | — | 100 | — | 96.8 | — | 3.0 | — | 0.2 |
| 4 | 13 X (a) | 400 | 5.7 | 100 | 100 | 98.1 | 96.3 | 1.9 | 3.7 | — | — |
| 5 | " | 375 | " | 100 | 100 | 98.0 | 96.8 | 2.0 | 3.2 | — | — |
| 6 | " | 350 | " | 100 | 100 | 99.0 | 97.3 | 1.0 | 2.7 | — | — |
| 7 | " | 325 | " | 100 | 100 | 97.4 | 96.4 | 2.6 | 3.6 | — | — |
| 8 | " | 300 | " | 100 | 100 | 97.0 | 95.1 | 3.0 | 4.9 | — | — |
| 9 | " | 275 | " | 100 | 100 | 93.6 | 92.1 | 6.4 | 7.9 | — | — |
| 10 | " | 400 | 11.4 | 100 | 100 | 97.7 | 96.2 | 2.3 | 3.8 | — | — |
| 11 | " | 325 | " | 100 | 97.5 | 95.4 | 95.1 | 4.6 | 4.9 | — | — |
| 12 | " | 270 | " | 100 | 100 | 96.0 | 93.4 | 4.0 | 6.6 | — | — |
| 13 | " | 250 | " | 100 | 100 | 94.7 | 91.7 | 5.3 | 9.3 | — | — |
| 14 | " | 230 | 2.8 | 100 | 95.7 | 95.1 | 91.2 | 4.9 | 9.8 | — | — |
| 15 | " | 200 | 2.8 | 100 | 64.0 | 95.0 | 90.0 | 5.0 | 10.0 | — | — |
| 17 (*) | Ca—Y | 400 | 5.7 | 97 | 55 | 98.3 | 98.2 | 1.7 | 1.8 | 0.2 | — |
| 18 | Ca—Na—Y (c) | 400 | " | 96 | 20 | 98.2 | 98.3 | 1.6 | 1.7 | — | — |
| 19 (**) | Co—Na Y (d) | 400 | " | 92 | 80 | 96.4 | 95.5 | 3.6 | 4.5 | — | — |

(a) Union Carbide;
(b) Davison;
(c) $Ca^{++}/Na^+$ molar ratio = 65/35;
(d) $Co^{++}/Na^+$ molar ratio = 70/30.
(*) Data survey after 1 h and 3 h.
(**) Data survey after 1 h and 4 h.

We claim:

1. A method for the synthesis of iodobenzene at 200°-500° C., characterized in that iodine, benzene and air or other gas containing molecular oxygen, are brought into contact, in the gaseous phase, with at least one zeolite of the X or the Y type, such zeolite having been exchanged with sodium.

2. A method for the synthesis of iodobenzene, characterized in that iodine, benzene and air or other gas containing molecular oxygen, are brought into contact, in the gaseous phase and at 300°-450° C., with at least one zeolite of the 13X or NaY type, the air:iodine ratio being higher than or equal to the stoichiometric ratio, the space velocity ranging from 1 to 20 Kg/h of benzene per Kg of pure zeolite, binder excluded, and said iodine being fed as a 5-20% by weight benzenic solution.

3. A method according to claim 2, wherein the air:iodine molar ratio is equal to or higher than 10.

4. A method according to claim 2, wherein the zeolite is partially exchanged with cobalt or with a rare earth metal.

5. A process according to claim 2, wherein said zeolite is a 13X zeolite.

6. A process according to claim 2, wherein said zeolite in a NaY zeolite.

7. A process according to claim 2, wherein the benzene:iodine molar ratio is from 10 to 30.

8. A method according to claim 2, wherein the zeolite is exchanged with sodium.

9. A method for the synthesis of iodobenzene, characterized in that iodine, benzene and air or other gas containing molecular oxygen, are brought into contact, in gaseous phase and at 300° C. to 450° C., with at least one zeolite of the 13X or NaY type, the air:iodine ratio being higher than or equal to the stoichiometric ratio, the space velocity ranging from 1 to 20 Kg/h of benzene per Kg of pure zeolite, binder excluded, said iodine being fed as a 5 to 20% by weight benzenic solution.

10. A method according to claim 9, wherein the air:iodine molar ratio is equal to or higher than 10.

11. A method according to claim 9, wherein the zeolite is partially exchanged with cobalt or with a rare earth metal.

* * * * *